United States Patent [19]

Carnell et al.

[11] Patent Number: 4,717,552

[45] Date of Patent: Jan. 5, 1988

[54] GAS PURIFICATION

[75] Inventors: Peter J. H. Carnell, Stockton-on-Tees; Patrick J. Denny, Croft-on-Tees, both of England

[73] Assignee: Imperial Chemical Industries PLC, London, England

[21] Appl. No.: 889,464

[22] Filed: Jul. 25, 1986

[30] Foreign Application Priority Data

Aug. 14, 1985 [GB] United Kingdom ............... 8520353

[51] Int. Cl.$^4$ .................. C01B 31/20; C01B 17/16
[52] U.S. Cl. ................................. 423/230; 55/35; 55/75
[58] Field of Search .................. 423/230; 55/35, 75

[56] References Cited

U.S. PATENT DOCUMENTS

| 4,358,297 | 11/1982 | Eberly | 423/230 |
| 4,374,654 | 2/1983 | McCoy | 423/230 |
| 4,522,793 | 6/1985 | Larson et al. | 423/230 |

FOREIGN PATENT DOCUMENTS

| 2650711 | 3/1976 | Fed. Rep. of Germany | 423/230 |
| 1568703 | 6/1980 | United Kingdom | 423/230 |
| 413968 | 3/1972 | U.S.S.R. | 423/230 |

Primary Examiner—John Doll
Assistant Examiner—Lori S. Freeman
Attorney, Agent, or Firm—Cushman, Darby & Cushman

[57] ABSTRACT

Desulphurization of natural gas is effected using a bed of particulate adsorbent comprising zinc oxide at below 30° C. before molecular sieve drying of the gas. The absorbent particles preferably have a high BET surface area and pore volume.

7 Claims, No Drawings

GAS PURIFICATION

This invention relates to gas purification and in particular to the desulphurisation and drying of natural gas.

Natural gas generally contains, in addition to hydrocarbons, small amounts of hydrogen sulphide and carbon dioxide. Also, particularly in gas obtained from offshore installations, it will often be saturated, or near saturated, with water vapour.

Before use, it is generally desirable to reduce the sulphur content of the gas to a low level.

As recovered from the drilling or borehole, the gas is normally a relatively low temperature, generally below 30° C. The precise temperature will depend on the locality. Thus gas from North Sea installations is typically at a temperature of 0° to 10° C., generally at about 4° C., but in some cases may be below 0° C., for example down to −10° C. Cooling of the gas, which may occur during cold weather and/or as a result of expansion of the gas as it passes constrictions in pipelines in some cases presents problems as a result of the deposition of the water vapour as ice. The deposited ice often has a volume many times that expected as a result of the occlusion of hydrocarbons in the ice forming so-called hydrocarbon hydrates. In severe cases this can lead to excessive pressure drops in pipelines and, in some cases, pipeline blockages.

It is generally not possible to heat the gas significantly, except perhaps as a result of compression, as such heating presents hazards, particularly in offshore installations, and anyway is economically unattractive.

For these reasons it is usual to subject the gas to a drying step to remove the bulk of the water vapour. The drying is conventionally effected by passing the gas through a suitable molecular sieve. However the molecular sieves tend to catalyse the formation of carbonyl sulphide from the carbon dioxide and hydrogen sulphide in the gas. While carbonyl sulphide can be removed, e.g. by an amine washing step or by absorption using a bed of a suitable absorbent material such as zinc oxide, amine washing steps are often undesirable as they also effect removal of carbon dioxide, which removal is often undesirable on economic grounds, while absorbent beds generally have only a poor capacity for carbonyl sulphide at low absorption temperatures.

In the present invention the hydrogen sulphide is removed prior to the drying stage so that little or no carbonyl sulphide is formed during passage of the gas through the molecular sieve.

Accordingly the present invention provides a process for the purification of natural gas containing water vapour and hydrogen sulphide comprising passing said gas at a temperature below 30° C. through a bed of pellets or granules of a solid material comprising zinc oxide and then drying said gas by passage through a molecular sieve.

The treatment temperature is preferably in the range −10° to +10° C.: of course the temperature should be such, in relation to the partial pressure of the water vapour in the gas, that the water does not separate as ice.

Heretofore hydrogen sulphide has been removed by an amine washing step as aforesaid and/or by passage through a zinc oxide bed at elevated temperature. Where the natural gas contains more than a few hundred, e.g. more than 300, ppm of hydrogen sulphide by volume, it may be desirable in the process of the invention to employ such an amine washing step, to provide a coarse removal of hydrogen sulphide, prior to passage through the zinc oxide bed, wherein the sulphur content of the natural gas is further reduced, in order to maximise the life of the zinc oxide bed.

The present invention avoids the need for heating the gas prior to passage through the zinc oxide bed.

The absorbent material preferably comprises at least 60, especially at least 80, % by weight of zinc oxide, calculated on the constituents of the absorbent material non-volatile at 900° C. As used in the process the zinc oxide may be, at least initially, wholly or partly hydrated or in the form of a salt of a weak acid, e.g. a carbonate.

The absorbent material is preferably in the form of porous agglomerates, as may be made, for example, by mixing a finely divided zinc composition with a cement binder and a little water, insufficient to give a slurry, and then granulated or extruded. In order to aid access of the gas stream into the particles, the latter may be provided in the form of extruded pellets having a plurality of through passages. Typically the BET surface area of the particles is at least 20, preferably in the range 50 to 200, $m^2.g^{-1}$, and the pore volume of the particles is preferably at least 0.2 $cm^3.g^{-1}$.

Since the absorption efficiency and hence the life of a zinc oxide particulate bed depends on the rate of diffusion of the zinc sulphide formed by reaction of the zinc oxide with the sulphur compounds towards the interior of the particle, particularly at low absorption temperatures, it is preferable to employ zinc oxide particles having a high pore volume, above 0.2 $cm^3.g^{-1}$ and high surface area, above 50 $m^2.g^{-1}$. Thus while zinc oxide particles having a lower pore volume and a surface area of the order of 25 to 30 $m^2.g^{-1}$ can be employed, the bed life at low absorption temperatures is relatively low, necessitating the use of large bed volumes to avoid premature break-through of the sulphur compounds into the exit gas stream. By using a bed of particles of pore volume above, for example, 0.25 $cm^3.g^{-1}$ and surface area above, for example, 70 $m^2.g^{-1}$, the bed volume can be markedly reduced, e.g. to about one third of that required with particles of low pore volume and surface area 25 to 30 $m^2.g^{-1}$. The particles employed thus preferably have a surface area above 50, particularly above 70, $m^2.g^{-1}$ and a pore volume above 0.25 $cm^3.g^{-1}$.

Preferred absorbent materials for the process have a hydrogen sulphide absorption capacity of at least 20, especially at least 25, % of the theoretical, at a temperature of 25° C., as determined in a standard test in which a mixture of hydrogen sulphide (2000 ppm by volume), carbon dioxide (4% by volume), and methane (balance) is passed through a bed of the particles at atmospheric presure and a space velocity of 700 $h^{-1}$ using a bed of circular cross section having a length to diameter ratio of 5.

A particularly suitable particulate zinc oxide material is that sold by Imperial Chemical Industries PLC as "Catalyst 75-1". These particles are granules typically having a surface area of the order of 80 $m^2.g^{-1}$ and a pore volume of about 0.3 $cm^3.g^{-1}$, and an adsorption capacity of about 27% of theoretical when measured by the above procedure.

After passage through the zinc oxide bed, the gas is dried, in the conventional manner, using a molecular sieve. Typical sieves includes sieves 3A, 4A, and 13X.

Where used in connection with an offshore installation, the process may be operated on the offshore platform or at the shore-based end of the pipeline therefrom before the wet gas is liable to be subject to significant cooling as a result of climatic conditions. Where there is a risk of cooling of the gas and ice deposition prior to reaching the shore, it is preferred that the process of the envention is operated on the offshore platform.

The invention is illustrated by the following example.

Granules of size approximately 3 to 5 mm of ICI "Catalyst 75-1" were charged to a tube of internal diameter 2.54 cm to form a vertical bed of length 12 cm. The bed thus had a volume of about 60 ml. Natural gas containing 1% by volume of hydrogen sulphide and having a water content of about 120 ppm by volume, was passed down through the bed at 25° C. and atmospheric pressure at a rate of 700 ml/min, (i.e. space velocity 700 h$^{-1}$).

The hydrogen sulphide content of the gas leaving the bed was monitored and when it rose to 1-2 ppm by volume, indicating that hydrogen sulphide "break-through" had occured, the flow of gas was stopped and the absorbent discharged from the bed.

The absorbent was discharged in six equal parts A to F, so that the distribution of sulphur down the depth of the bed could be determined, and each part analysed for its sulphur content. The results are shown in the following table.

| Bed portion | Sulphur content of discharged absorbent (% w/w) |
| --- | --- |
| A (top) | 9.0 |
| B | 9.6 |
| C | 9.4 |
| D | 8.5 |
| E | 6.5 |
| F (bottom) | 2.5 |
| AVERAGE | 7.6 |
| Time to "break-through" | 4 hours |

We claim:

1. A process for the purification of natural gas containing water vapour, carbon dioxide and hydrogen sulphide comprising passing said gas at a temperature below 30° C. through a bed of pellets or granules of a solid material comprising zinc oxide and then drying said gas by passage through a molecular sieve.

2. A process according to claim 1 wherein the gas is passed through the bed at a temperature in the range −10° to +10° C.

3. A process according to claim 1 wherein the gas contains up to 300 ppm by volume of hydrogen sulphide.

4. A process according to claim 1 wherein the absorbent material comprises at least 80% by weight of zinc oxide, calculated on the constituents non-volatile at 900° C.

5. A process according to claim 1 wherein the absorbent material has a BET surface area in the range 50 to 200 m$^2$.g$^{-1}$ and a pore volume of at least 0.2 cm$^3$.g$^{-1}$.

6. A process according to claim 5 wherein the absorbent material has a BET surface area of at least 70 m$^2$.g$^{-1}$ and a pore volume of at least 0.25 cm$^3$.g$^{-1}$.

7. A process according to claim 1 wherein the absorbent material has a hydrogen sulphide absorption capacity of at least 25% of theoretical at 25° C.

* * * * *